US012465532B2

(12) United States Patent
Arai

(10) Patent No.: US 12,465,532 B2
(45) Date of Patent: Nov. 11, 2025

(54) UNDERPANTS-TYPE DISPOSABLE WEARING ARTICLE

(71) Applicant: DAIO PAPER CORPORATION, Shikokuchuo (JP)

(72) Inventor: Hiroki Arai, Tochigi (JP)

(73) Assignee: Daio Paper Corporation, Ehime (JP)

( * ) Notice: Subject to any disclaimer, the term of this patent is extended or adjusted under 35 U.S.C. 154(b) by 416 days.

(21) Appl. No.: 17/997,970

(22) PCT Filed: May 25, 2021

(86) PCT No.: PCT/JP2021/019763
§ 371 (c)(1),
(2) Date: Apr. 13, 2023

(87) PCT Pub. No.: WO2022/004195
PCT Pub. Date: Jan. 6, 2022

(65) Prior Publication Data
US 2023/0248587 A1 Aug. 10, 2023

(30) Foreign Application Priority Data
Jul. 3, 2020 (JP) ................................ 2020-115703

(51) Int. Cl.
*A61F 13/496* (2006.01)

(52) U.S. Cl.
CPC ................................ *A61F 13/4963* (2013.01)

(58) Field of Classification Search
CPC ................ A61F 13/496; A61F 13/4963; A61F 2013/00812; A61F 13/49058–49061; A61F 2013/49063–49087
See application file for complete search history.

(56) References Cited

U.S. PATENT DOCUMENTS

2004/0186451 A1* 9/2004 Bishop ................ A61F 13/5655 604/385.11
2018/0280209 A1 10/2018 Manabe

FOREIGN PATENT DOCUMENTS

CN 108024881 A 5/2018
JP H0428363 A 1/1992
JP H11332913 A 12/1999
JP 2002035029 A 2/2002
(Continued)

OTHER PUBLICATIONS

International Search Report for PCT/JP2021/019763, mailed Jul. 6, 2021.
(Continued)

*Primary Examiner* — Susan S Su
(74) *Attorney, Agent, or Firm* — Andrus Intellectual Property Law, LLP

(57) ABSTRACT

Underpants-type disposable wearing articles are provided wherein transverse tearing is hard to develop at a stacked sheet number change part in the outer member. This problem is solved by an underpants-type disposable wearing article, in which cuts 61 each extending longitudinally across a stacked sheet number change part 62 where the number of stacked sheets constituting the outer member 20 varies are formed adjacent on the central side in the width direction of a side seal 21 formed by joining the front and body sections together along the opposed lateral portions, and which is free of a perforated line formed from the waist opening toward the leg opening.

7 Claims, 10 Drawing Sheets

(56) References Cited

FOREIGN PATENT DOCUMENTS

| | | | | |
|---|---|---|---|---|
| JP | 2002178428 | A | 6/2002 | |
| JP | 2002273808 | A | 9/2002 | |
| JP | 2010131193 | A | 6/2010 | |
| JP | 4522469 | B2 | 8/2010 | |
| JP | 2011234847 | A | 11/2011 | |
| JP | 2012070917 | A | 4/2012 | |
| JP | 2013233382 | A | 11/2013 | |
| JP | 2015092957 | A | 5/2015 | |
| JP | 2017064130 | A | 4/2017 | |
| JP | 2017225847 | A | 12/2017 | |
| JP | 2018061545 | A | 4/2018 | |
| JP | 2018139718 | A | 9/2018 | |
| WO | WO-2017002217 | A1 * | 1/2017 | ........ A61F 13/49011 |

OTHER PUBLICATIONS

First Office Action for CN Patent Appl. No. 202180030464.5, dated Jun. 28, 2025.

* cited by examiner

[FIG.1]
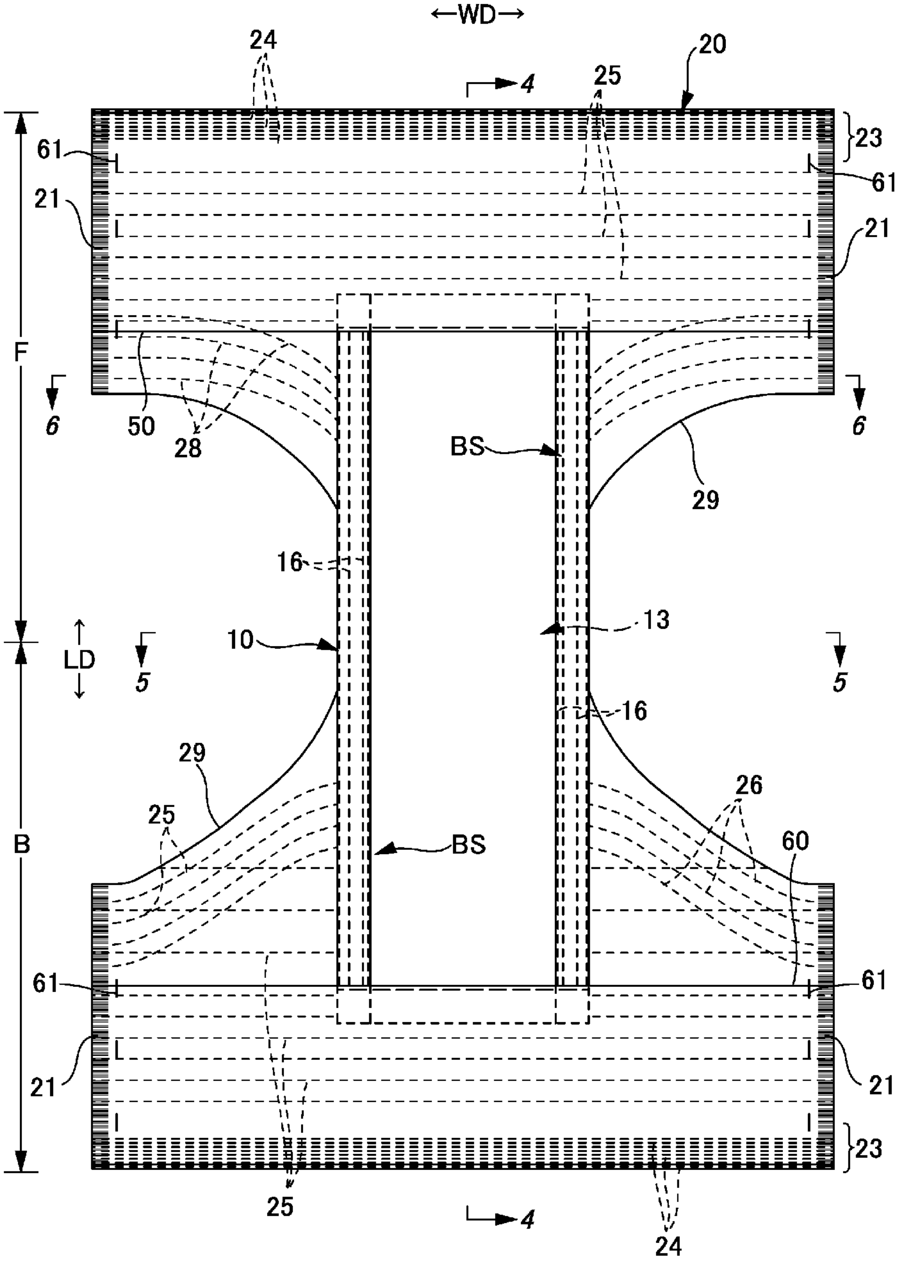

[FIG.2]
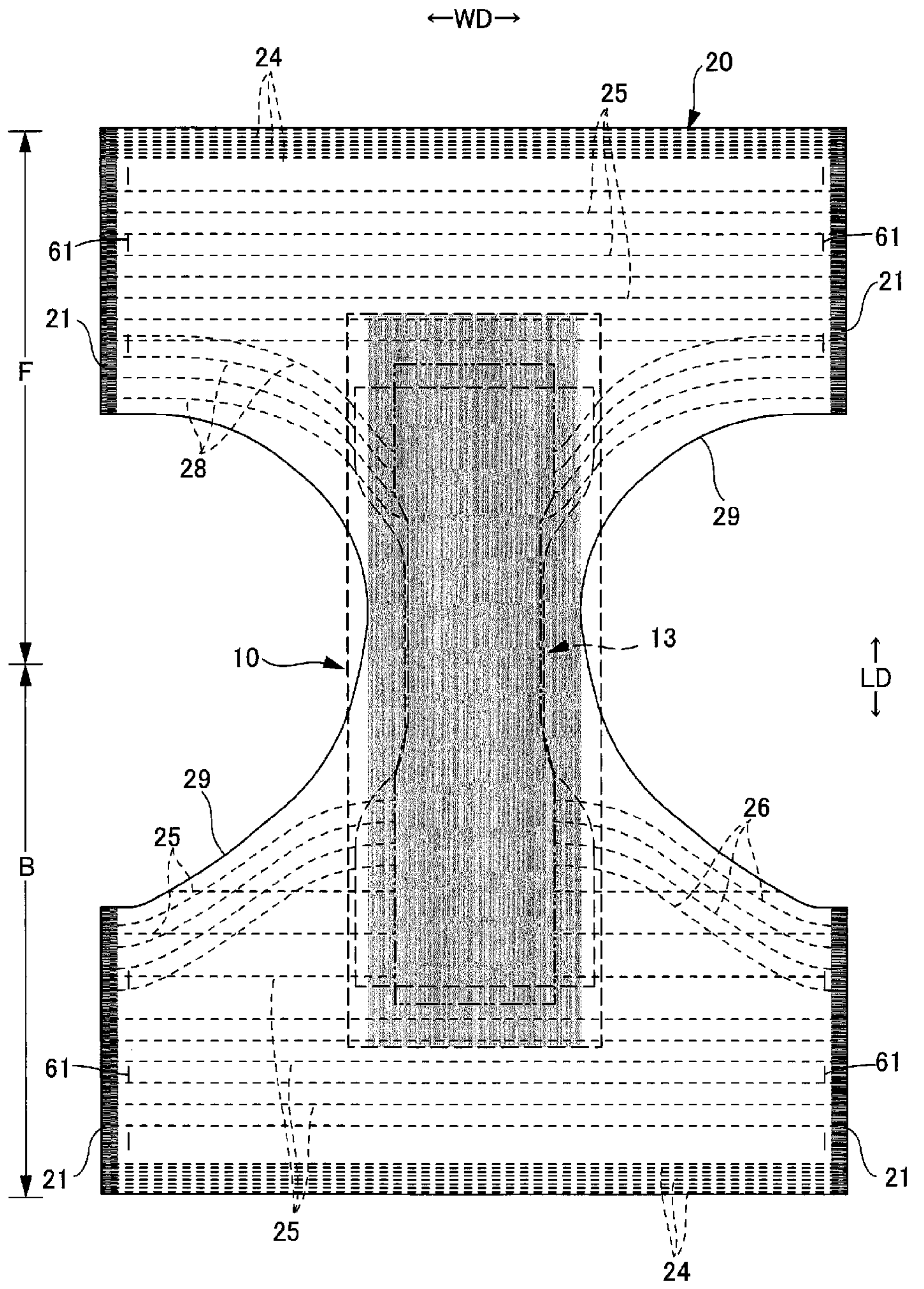

[FIG.3]
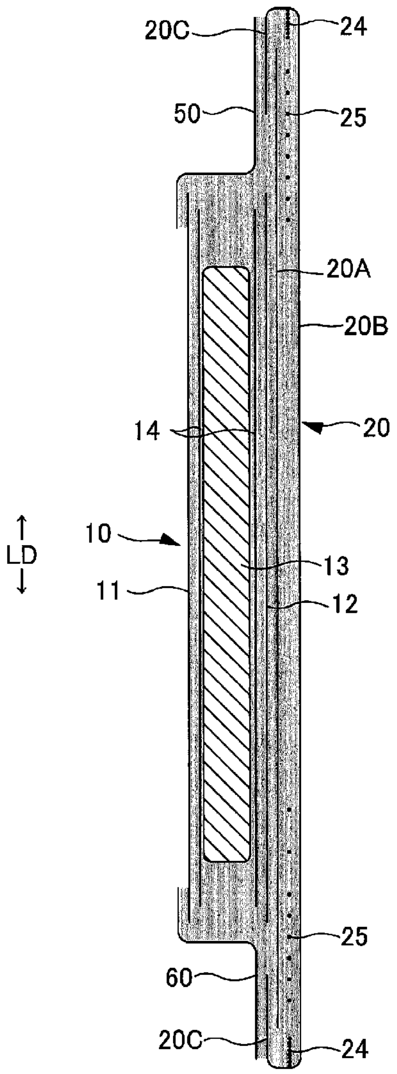

[FIG.4]
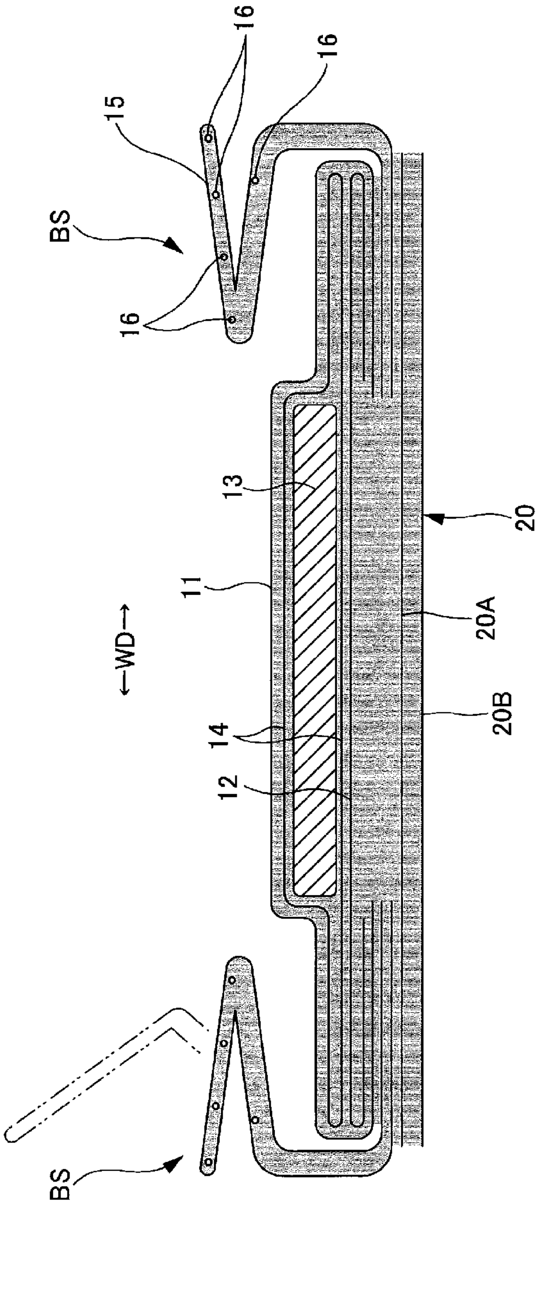

[FIG.5]
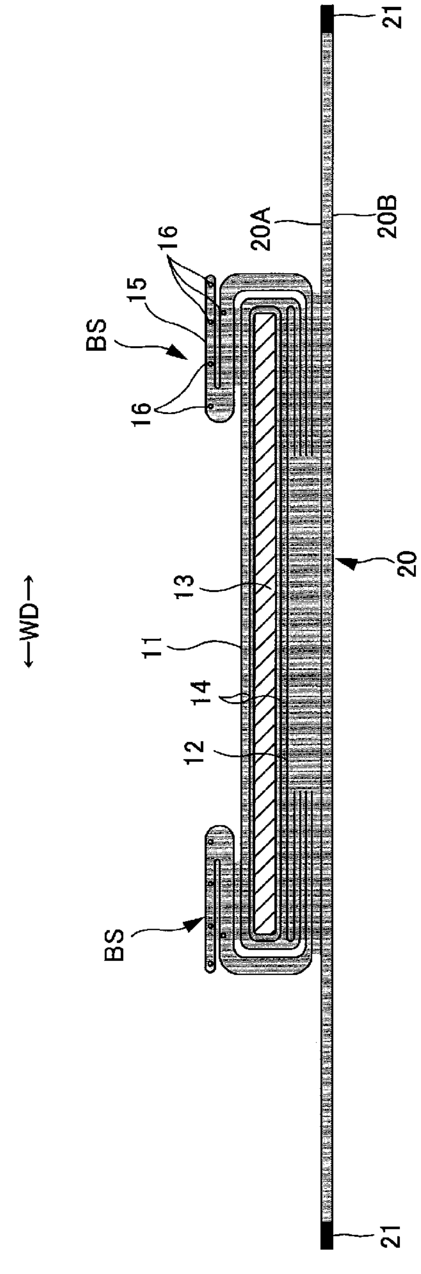

【FIG.6】
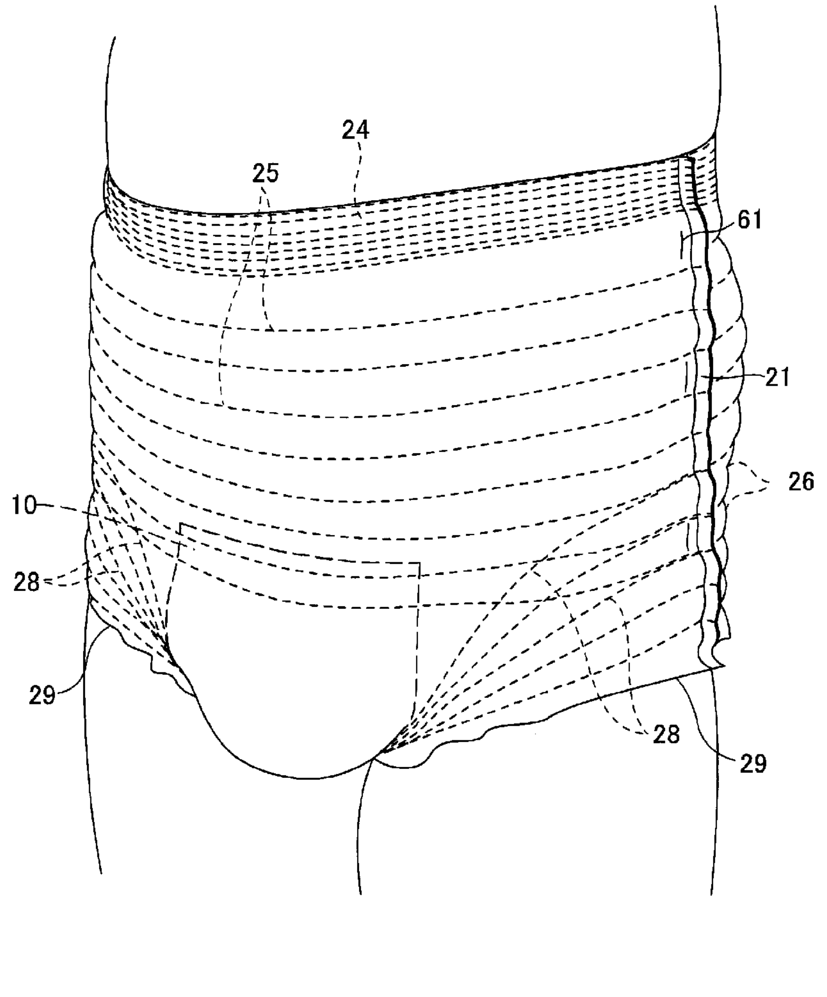

[FIG.7]
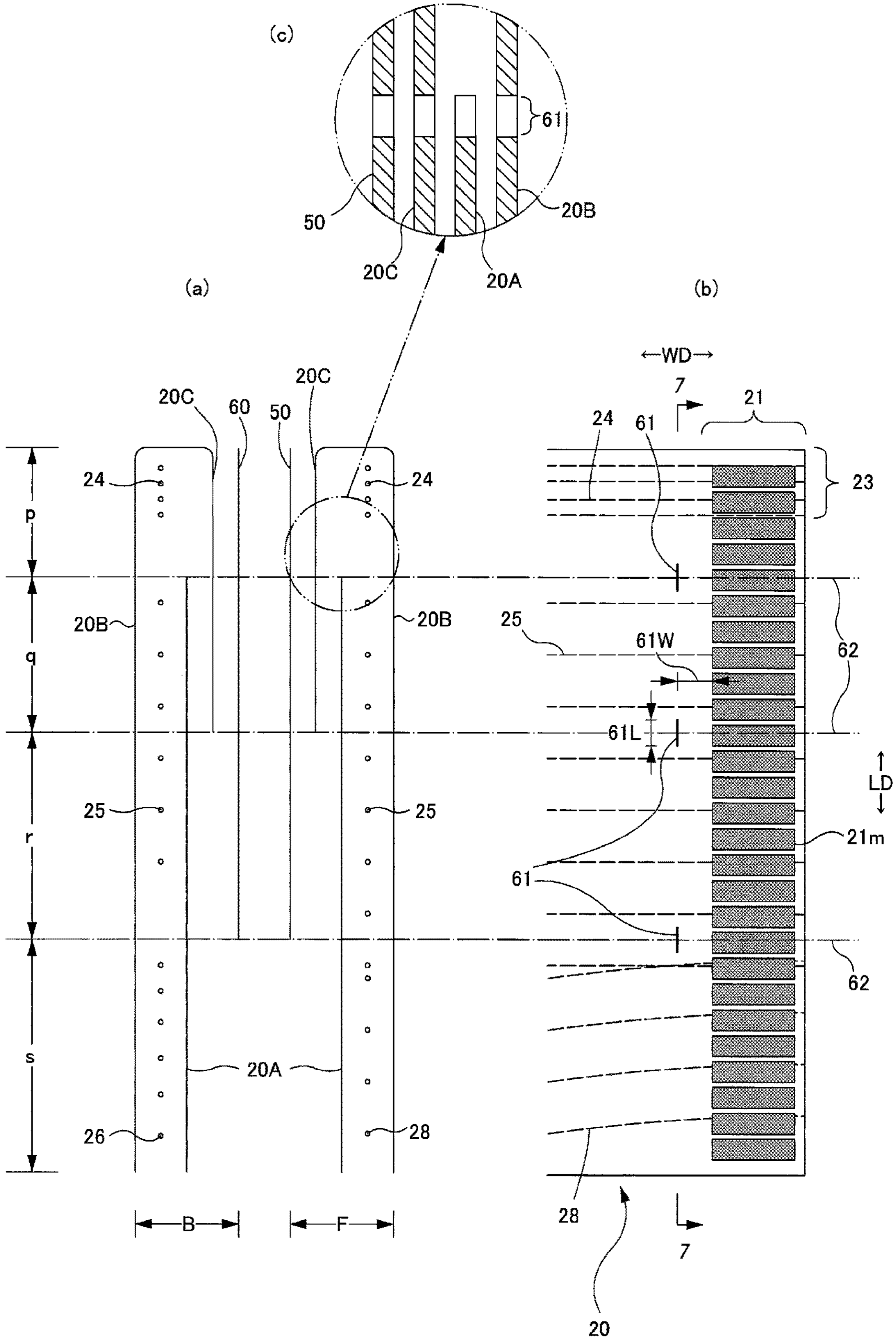

[FIG.8]
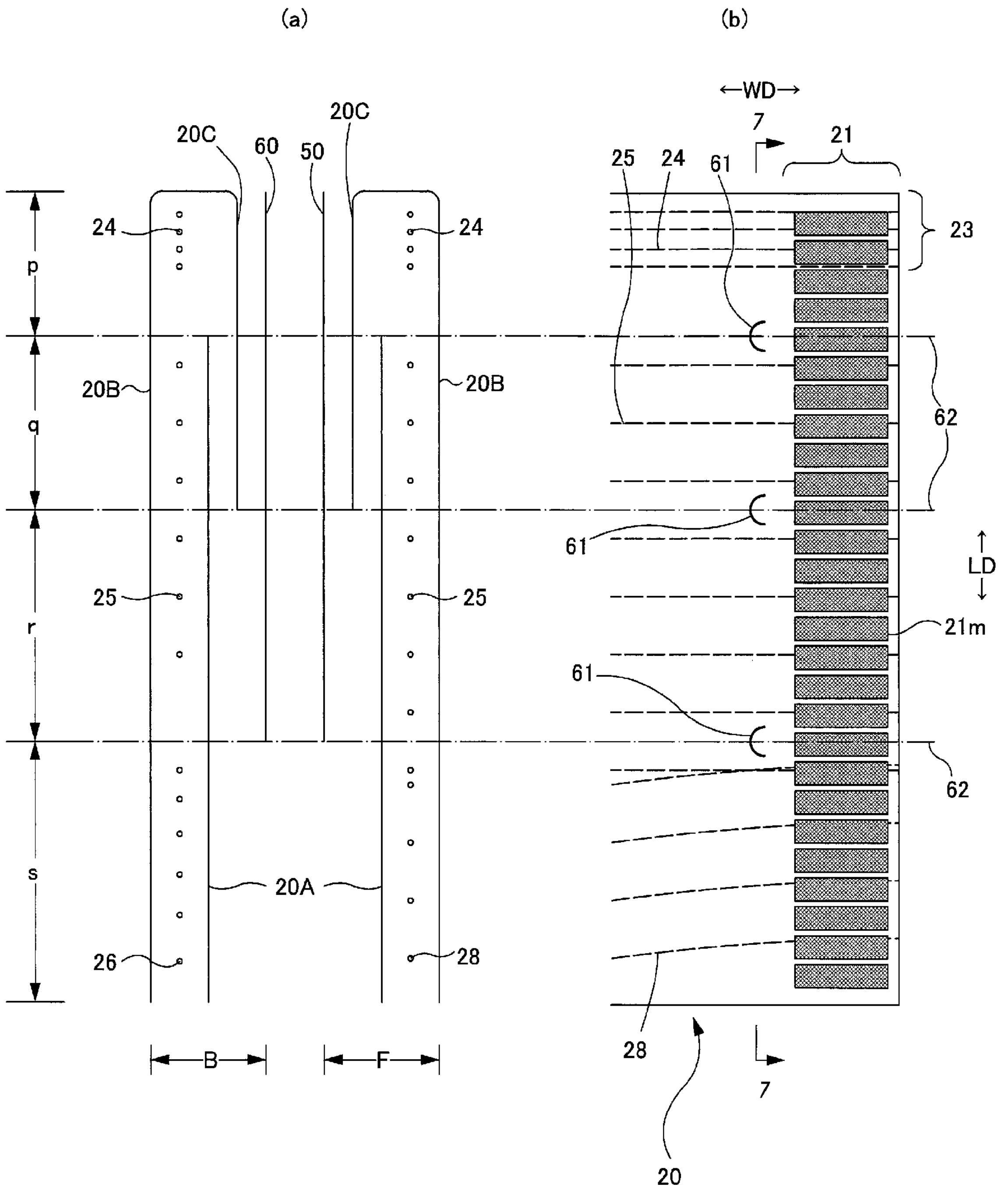

[FIG.9]
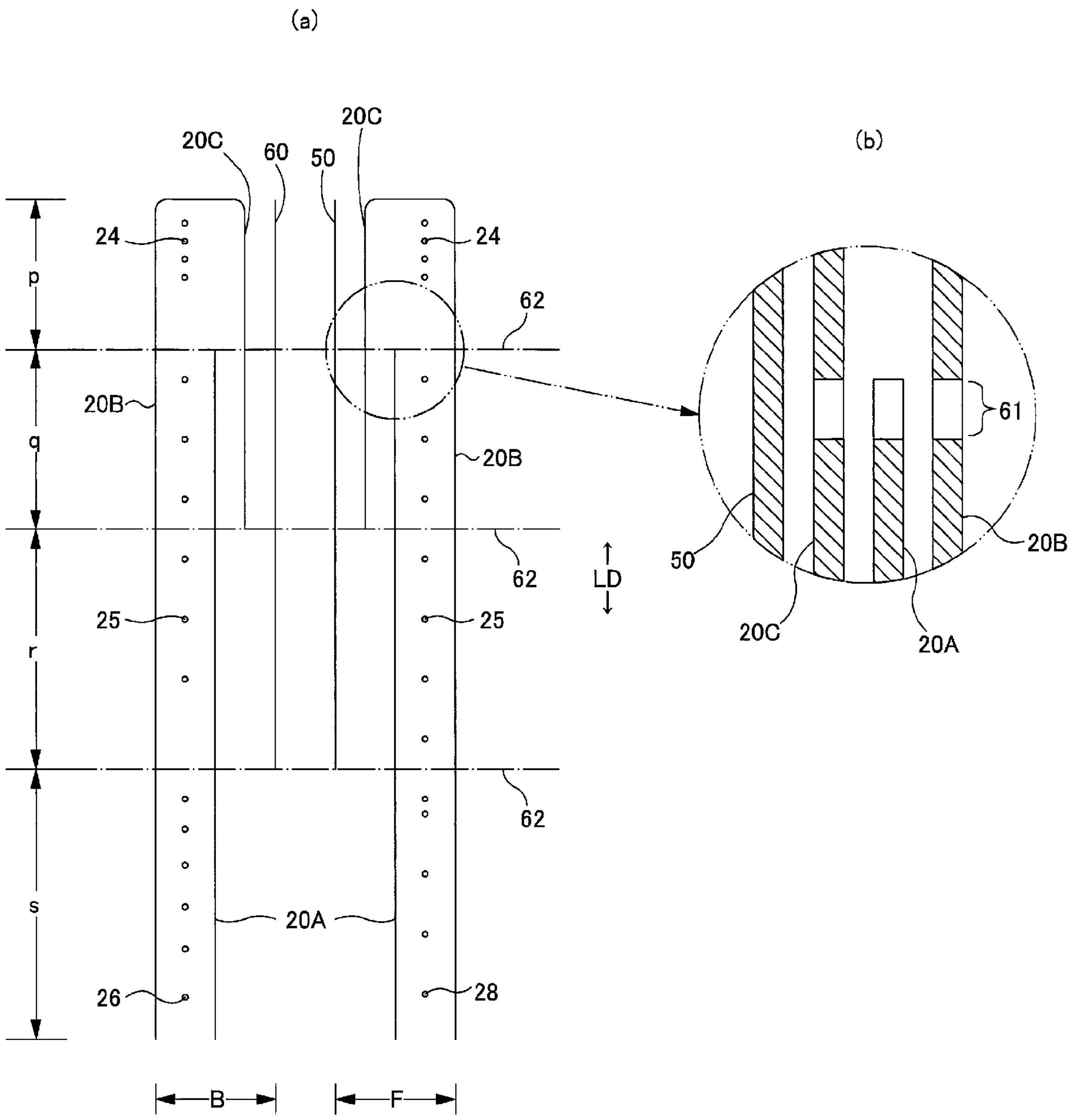

[FIG.10]
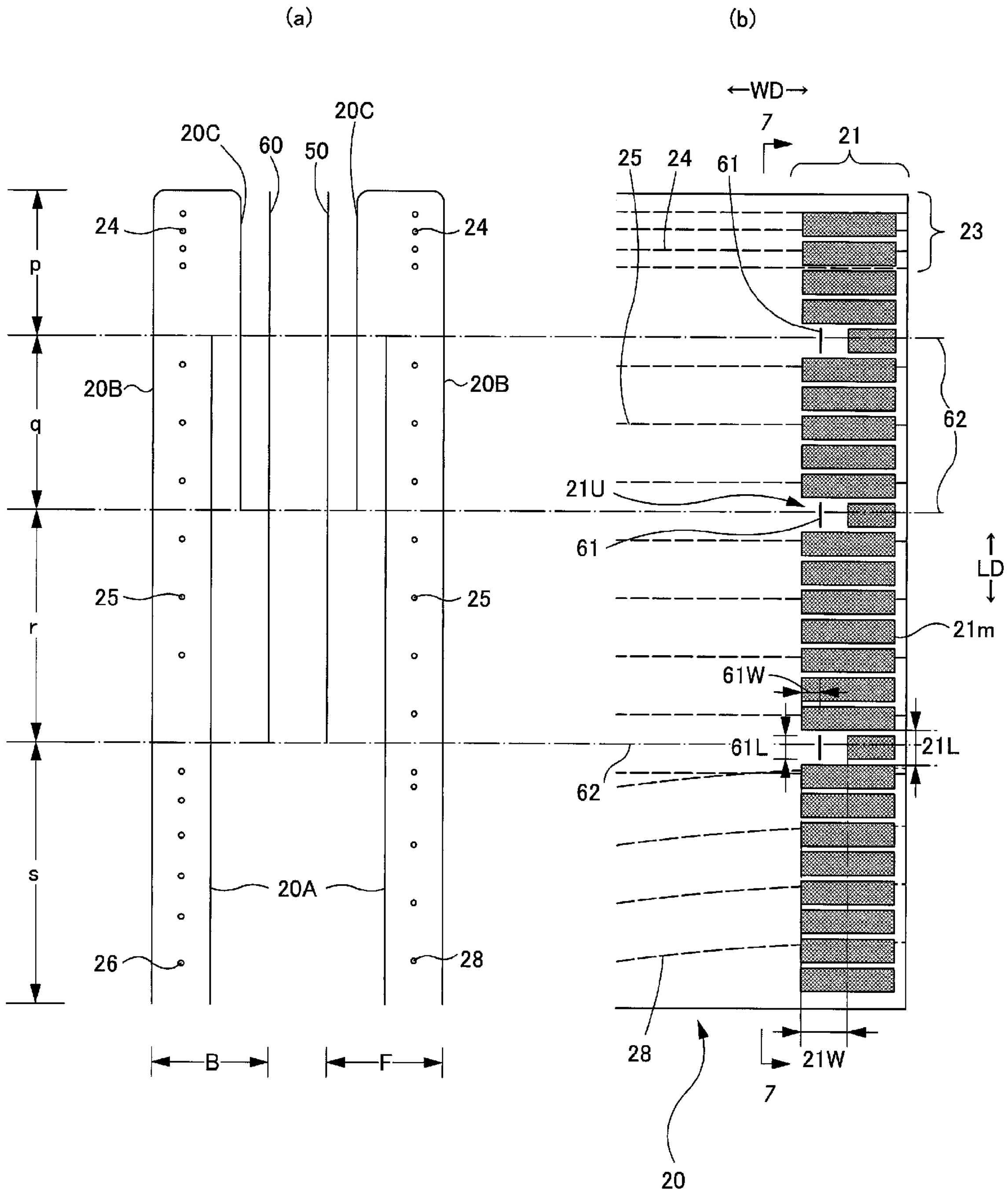

UNDERPANTS-TYPE DISPOSABLE WEARING ARTICLE

CROSS-REFERENCE TO RELATED APPLICATIONS

This application is the U.S. national stage application of International Application PCT/JP2021/019763, filed May 25, 2021, which international application was published on Jan. 6, 2022, as International Publication WO 2022/004195 in the Japanese language. The International Application claims priority of Japanese Patent Application No. 2020-115703, filed Jul. 3, 2020. The international application and Japanese application are both incorporated herein by reference, in entirety.

FIELD OF ART

The present invention relates to underpants-type disposable wearing articles.

BACKGROUND ART

Underpants-type disposable wearing articles, such as underpants-type disposable diapers, underpants-type disposable sanitary napkins, and underpants-type disposable diaper covers, have a front body and a back body joined together along their opposed lateral portions by melt-bonding to form opposed side seals, which results in advance formation of a waist opening and leg openings.

With such an underpants-type disposable diaper, upon taking the diaper off the wearer after excretion or the like, the side seals are torn for removing the diaper from the body. Accordingly, the side seals are required to have not only a sufficient peel strength for resisting tearing during wearing, but also tearability after use (see, e.g., Patent Publications 1 and 2). Here, tearing of the side seals includes tearing off, wherein one of the front and back body sections is broken along the edge of each side seal on the central side in the width direction, ripping down, wherein the melt-bonding between the front and back bodies is subjected to interfacial peeling, and combinations thereof.

Various factors are conceivable in limiting the side seal tearability, and one of the particularly important factors may be the number of sheets staked in the side seals, varying in the direction of tearing. That is, in a stacked sheet number change part in the side seals, wherein the number of stacked sheets varies (in particular, the position wherein the number of stacked sheets varies from smaller to larger), the tearing tends to proceed more easily along the boundary where the number of stacks changes than longitudinally, so that so-called transverse tearing may occur, wherein the tearing develops from the stacked sheet number change part toward the center in the width direction.

As one means for solving this problem, there is proposed to form a perforated line in the front or back body section on the central side in the width direction of each side seal for splitting the body section from the waist opening over to a leg opening, rather than to improve the joining pattern of the side seals (see Patent Publication 3).

For facilitating commencement of tearing of the perforated line, however, it is necessary to provide a notch that reaches the edge of the waist opening or the edge of a leg opening (see FIGS. 4, 10, 11, and the like), and this notch at the beginning of the perforated line may deteriorate the fitting. In contrast, commencement of tearing of the conventional side seals is quite easy as the force is naturally applied at the edges of the joined areas.

Further, formation of the perforated lines from the waist opening over to the leg openings may result in a large number of cuts in the perforated lines, which may cause likeliness of leakage or deterioration of appearance.

PRIOR ART PUBLICATION

Patent Publication

Patent Publication 1: JP 2018-061545 A
Patent Publication 2: JP 4522469 B
Patent Publication 3: JP 2018-139718 A

SUMMARY OF THE INVENTION

Problem to be Solved by the Invention

It is therefore a primary object of the present invention to reduce tendency of transverse tearing in the position where the number of stacked sheets varies, without formation of perforated split lines from the waist opening over to the leg openings.

Means for Solving the Problem

The underpants-type disposable wearing articles which solve the problem are as follows.

First Aspect

An underpants-type disposable wearing article, including:
- a front body section and a back body section,
- opposed side seals formed by joining the front body section and the back body section together along opposed lateral portions by means of melt-bonding,
- a waist zone cylindrically continuous via the side seals,
- a waist opening, which is an opening on a waist side of the waist zone, and
- a pair of right and left leg openings located closer to legs than the waist zone,
- wherein the front body section and the back body section are formed by bonding a plurality of sheet layers,
- each side seal and area adjacent on a central side in a width direction thereof have at least one stacked sheet number change part where a number of stacked sheets varies from a waist opening side toward a leg openings side,
- wherein a cut extending longitudinally across one stacked sheet number change part is formed adjacent on the central side in the width direction of each side seal in the sheet layers forming at least either the front body section or the back body section, and
- wherein the disposable article is free of a perforated line intended for splitting from the waist opening to a leg opening.

Effect

According to the present underpants-type disposable wearable article, in tearing the side seals from the waist opening downwards to leg openings, or in reverse upwards, even when the position where the number of the stacked sheet layers varies is reached and transverse tearing is developing, the transverse tearing, upon reaching the cut, turns its direction longitudinally to proceed in the longitudinal direction. Accordingly, the transverse tearing may be avoided effectively in tearing the side seals.

Second Aspect

The underpants-type disposable wearing article according to the first aspect, wherein each cut is configured to extend closer to the side seal with increasing proximity to its longitudinal ends.

Effect

When the cuts are in such a shape as in the present aspect, for example, in a doglegged or semicircular shape, irrespective of whether the tearing of the side seals are commenced downwards or upwards, when transverse tearing is developed at a stacked sheet number change part and reaches the cut, the direction of the transverse tearing is guided back toward the side seal, to further facilitate continuous longitudinal tearing along the side seal.

Third Aspect

The underpants-type disposable wearing article according to the first or second aspect, wherein the cuts consist of cuts each penetrating all but one of the plurality of sheet layers constituting the front body section or the back body section.

Effect

According to the present aspect, not only leakage through the cuts, but also appearance of the skin of the wearer through the cuts when the article is worn, is avoided, so that the cuts are not apparent and the appearance is improved.

Fourth Aspect

The underpants-type disposable wearing article according to any one of first to third aspects, wherein a dent concaved laterally is formed in a side edge of each side seal on the central side in the width direction so as to cross longitudinally one stacked sheet number change part, and wherein each cut is formed in each dent.

Effect

Having the cut in each dent in the side seals means that the cuts are positioned within the entire width of each side seal, so that the cuts are hard to be brought into contact with the skin of the wearer, which may avoid deterioration of the fitting. In addition, the cuts are not apparent and the appearance when the article is worn is improved.

Effect of the Invention

According to the present invention, tendency of transverse tearing in a position where the number of stacked sheets varies may be reduced without perforated split lines formed from the waist opening over to leg openings.

BRIEF DESCRIPTION OF THE DRAWINGS

FIG. 1 is a plan view (interior face) of an underpants-type disposable diaper in its spread state.

FIG. 2 is a plan view (exterior face) of the underpants-type disposable diaper in its spread state.

FIG. 3 is a sectional view taken along lines 4-4 in FIG. 1.

FIG. 4 is a cross sectional view taken along lines 5-5 in FIG. 1.

FIG. 5 is a cross sectional view taken along lines 6-6 in FIG. 1.

FIG. 6 is a perspective view of the underpants-type disposable diaper in a worn state.

FIG. 7 shows schematic views of the cuts according to the first embodiment, wherein FIG. 7(*a*) is a sectional view taken along lines 7-7, FIG. 7(*b*) is a view, seen from the ventral side, of the vicinity of the cuts in the underpants-type disposable diaper, and FIG. 7(*c*) is an enlarged sectional view of the vicinity of the cut in the sectional view taken along lines 7-7.

FIG. 8 shows schematic views of the cuts according to the second embodiment, wherein FIG. 8(*a*) is a sectional view taken along lines 7-7, and FIG. 8(*b*) is a view, seen from the ventral side, of the vicinity of the cuts in the underpants-type disposable diaper.

FIG. 9 shows schematic views of the cuts according to the third embodiment, wherein FIG. 9(*a*) is a sectional view taken along lines 7-7, and FIG. 9(*b*) is an enlarged sectional view of the vicinity of the cut in the sectional view taken along lines 7-7.

FIG. 10 shows schematic views of the cuts according to the fourth embodiment, wherein FIG. 10(*a*) is a sectional view taken along lines 7-7, and FIG. 10(*b*) is a view, seen from the ventral side, of the vicinity of the cuts in the underpants-type disposable diaper.

EMBODIMENTS FOR CARRYING OUT THE INVENTION

An underpants-type disposable diaper as an embodiment of absorbent articles will now be discussed with reference to the attached drawings.

FIGS. 1 to 6 show an underpants-type disposable diaper. This underpants-type disposable diaper (also referred to simply as the diaper hereinbelow) has an outer member 20 defining a front body section F and a back body section B, and an inner member 10 fixed on the interior face of the outer member 20 from the front body section F over to the back body section B, wherein the inner member 10 is composed of a liquid-pervious top sheet 11, a liquid-impervious sheet 12, and an absorber body 13 interposed therebetween. In production, the under face of the inner member 10 is fixed to the interior face (top face) of the outer member 20 with joining means, such as a hot melt adhesive (dotted pattern area in FIG. 2), then the inner member 10 and the outer member 20 together are folded along the transverse line passing the center in the front-back direction (longitudinal direction), forming the border between the front body section F and the back body section B, and the front body section and the back body section are joined together along the opposed lateral portions by means of melt-bonding to form opposed side seals 21, resulting in an underpants-type disposable diaper having a waist opening and a pair of right and left leg openings defined therein. The side seals have a particular pattern of melt-bonded areas 21*m* in the form of dots or rectangles arranged therein.

Example of Inner Member Structure

The inner member 10 has a structure including, as shown in FIG. 3, a top sheet 11, a liquid-impervious sheet 12, and an absorber body 13 interposed therebetween, and absorbs and contains excreted liquid permeated through the top sheet 11 in the absorber body 13. The plan shape of the inner member 10 is not particularly limited, and is usually a generally rectangular shape as in the illustrated embodiment.

The absorber body 13 may have a single-layered structure as shown in FIGS. 3 to 5, or a multi-layered structure. The absorber body 13 may be a commonly-known absorber, for example, an accumulation of pulp fibers, an assembly of filaments, such as of cellulose acetate, or nonwoven fabric, to which a superabsorbent polymer is mixed, fixed, or otherwise, as required. The absorber body 13 may be packaged with a liquid-pervious liquid-retaining packing sheet 14, such as of crepe paper, as required, for retaining its shape and holding the polymer therein. The absorber body 13 is in the shape of an hourglass having a narrower portion with a smaller width in the crotch section compared to the width of the portions forward and backward thereof, but may otherwise be in a suitable shape, such as a rectangular shape.

The top sheet 11 covering the top side (on the side of the face to be in contact with the skin) of the absorber body 13 may preferably be formed of perforated or non-perforated nonwoven fabric or porous plastic sheet. The raw material fibers constituting the nonwoven fabric may be synthetic fibers, such as polyolefin-based including polyethylene or polypropylene, polyester-based, or polyamide-based fibers, recycled fibers, such as rayon or cupra, or natural fibers, such as cotton, and the nonwoven fabric may have been produced through suitable processing, such as spunlacing, spunbonding, thermal bonding, melt-blowing, or needle punching. Among these processing methods, the spunlacing is superior in imparting flexibility and draping properties, whereas the thermal bonding is superior in imparting bulkiness and softness. With a number of through holes formed through the top sheet 11, urine or the like may rapidly be absorbed.

The liquid-impervious sheet 12 covering the underside (on the side of the face out of contact with the skin) of the absorber body 13 may be formed of a liquid-impervious sheet of plastic, such as polyethylene or polypropylene, and those having moisture-permeability are preferably used recently for preventing dampness. Such liquid-impervious, moisture-permeable sheet may be a microporous sheet obtained by kneading an inorganic filler, such as of calcium carbonate, in a polyolefin-based resin, such as polyethylene or polypropylene, in a molten state, forming the resulting mixture into a sheet, and then uni- or biaxially drawing the sheet. In the illustrated embodiment, the liquid-impervious sheet 12, together with the top sheet 11, is folded back in the lateral portions opposed in the width direction of the absorber body 13 onto the underside, but is not limited to such a structure and may adopt any other known structure.

On each lateral portion of the inner member 10, a three-dimensional gather part BS which mainly fits on and around each leg is provided. Each three-dimensional gather part BS has a fixed portion fixed on the under face of the inner member 10 in its lateral portion, a main body portion extending from the fixed portion around the lateral side of the inner member 10 onto the top face of the inner member 10 in its lateral portion, laid-down portions formed by fixing the front and back end portions, respectively, of the main body portion in a laid down state to the top face of the inner member 10 in its lateral portion, and a free portion formed by unfixing the zone between the laid-down portions of the main body portion. These portions are formed from a gathered sheet 15 which has been formed into a duplicate sheet by folding. Between the layers of the duplicate sheet, elongate gathering elastic members 16 are arranged in the free edge area or the like of the free portion. With such a structure of the three-dimensional gather parts BS, the free portions, which project in the opposed lateral portions of the absorber body, are raised in the product state with the contraction of the gathering elastic members 16. The gathered sheet 15 may preferably be formed of nonwoven fabric which has been rendered water-repelling.

Each gathering elastic member 16 may be made of a material that is usually used, for example, polystyrene rubber, polyolefin rubber, polyurethane rubber, polyester rubber, polyurethane, polyethylene, polystyrene, styrene-butadiene copolymer, silicone, or polyester. The gathering elastic members, for making them hardly observable from outside, may preferably have a fineness of 925 dtex or less and are arranged at a tension of 150 to 350% and at intervals of 7.0 mm or less. In addition, the gathering elastic members 16 may be in the form of strings as in the illustrated embodiments, or in the form of tapes having a certain width.

The raw material fibers of the nonwoven fabric constituting the gathered sheet 15 may also be, like the top sheet 11, synthetic fibers, such as polyolefin-based including polyethylene or polypropylene, polyester-based, or polyamide-based fibers, recycled fibers, such as rayon or cupra, or natural fibers, such as cotton, and the nonwoven fabric may have been produced through suitable processing, such as spunlacing, spunbonding, thermal bonding, melt-blowing, or needle punching. For preventing dampness, nonwoven fabric with a reduced basis weight for improved air-permeability may preferably be used. Further, the gathered sheet 15 may preferably be formed from a water-repelling nonwoven fabric with a coating of a silicone-, paraffin-metal-, or alkyl chromic chloride-based water repelling agent for preventing permeation of urine or the like as well as for preventing rash and improving a touch to the skin (dryness).

Example of Outer Member Structure

The outer member 20 as shown in FIGS. 3 to 5 has a presser sheet 20A and a backing sheet 20B, each made of nonwoven fabric or the like, and also elastic members 24 to 28 arranged between the presser sheet 20A and the backing sheet 20B as well as between the layers of the backing sheet 20B in a folded portion 20C formed by folding the backing sheet 20B onto the interior face along the edge of the waist opening. The outer member 20 is contracted under the contraction force of the elastic members in the natural length state, whereby stretchability is imparted. The planar shape is generally an hourglass shape having centrally-curved round-leg lines 29 provided in the opposed lateral portions in the middle for forming leg openings.

The outer member 20 in the illustrated embodiment is provided with elastic members, which are, in the spread state as shown in FIGS. 1 and 2, waist elastic members 24 located in the vicinity 23 of the waist opening, a plurality of under-waist elastic members 25 arranged at longitudinal intervals, each extending in the width direction, and a plurality of curved elastic members 26, 28 arranged at intervals without intersection, each extending in a curved manner from one of the opposed side seals 21 along one of the leg openings, across the crotch section, further along the other of the leg openings up to the other of the side seals 21, in each of the front body section F and the back body section B separately from a group of the under-waist elastic members 25. These elastic members 24 to 28 are each fixed in a stretched state at a particular stretch rate along the respective direction of extension. Incidentally, in the present outer member 20, elastic members are not provided which extend from one of the side seals in the front body section F along the corresponding round-leg line 29 up to the side seal in the back body section B.

The waist elastic members 24 are in the form of a plurality of elongate elastic members, such as rubber threads, arranged at longitudinal intervals in the vicinity of the waist opening edge in the region between the opposed side seals 21 joining the front body section F and the back body section B, and produce stretching/contracting force to constrict the body in the waist zone for fitting the diaper on the body. The waist elastic members 24, which are rubber threads in the illustrated embodiment, may be, for example, a stretchable member in the form of a tape. Further, the waist elastic members 24, which are held between the layers of the doubled nonwoven fabric sheet in the folded portion 20C of the backing sheet 20B in the waist zone in the illustrated embodiment, may be held between the presser sheet 20A and the backing sheet 20B.

The under-waist elastic members 25 are in the form of elongate elastic members, such as rubber threads, arranged at longitudinal intervals within the front-back extension between the opposed side seals 21, and impart stretching/contracting force in the width direction in the under-waist zones of the front body section F and the back body section B for bringing the diaper into close contact with the body. The waist elastic members 24 and the under-waist elastic members 25 may not necessarily be clearly divided along a boundary. For example, it suffices that, among the elastic members arranged at longitudinal intervals, each extending in the width direction, in the front body section F and in the back body section B, some elastic members from the upper side, though the number may not be specified, function as the waist elastic members, while the remaining elastic members function as the under-wait elastic members.

In the back body section B, dorsal curved elastic members 26 provided separately from the under-waist elastic members 25 are in the form of elongate elastic members, such as rubber threads, and arranged along predetermined curved lines. Only one dorsal curved elastic member 26 may be provided, but preferably a plurality of them is provided, and in the illustrated embodiment, four elongate elastic members, such as rubber threads, are provided, and these dorsal curved elastic members 26 are arranged at intervals without intersection. These dorsal curved elastic members 26 are not provided substantially as a bunch of about two or three elastic members arranged at close intervals, but preferably three or more of them are arranged at intervals of 3 to 20 mm, preferably about 6 to 16 mm, to form a predetermined stretchable/contractible zone.

In the front body section F of the outer member 20, ventral curved elastic members 28 provided separately from the under-waist elastic members 25 are in the form of elongate elastic members, such as rubber threads, and arranged along predetermined curved lines. Only one ventral curved elastic member 28 may be provided, but preferably a plurality of them is provided, and in the illustrated embodiment, four thread-like elastic members are provided, and these ventral curved elastic members 28 are arranged at intervals without intersection. These ventral curved elastic members 28 are not provided substantially as a bunch of about two to three elastic members arranged at close intervals, but preferably three or more of them are arranged at intervals of 3 to 20 mm, preferably about 6 to 16 mm, to form a predetermined stretchable/contractible zone.

Note that, as shown in FIG. 2, during manufacture, each of the under-waist elastic members 25 and the curved elastic members 26, 28 arranged in the front body section F and in the back body section B may be unintermittently fixed to the outer member 20, and then finely cut in a predetermined cutting pattern in the middle portion in the width direction of the area that overlaps the absorber body 13 (the area encircled by chain double-dashed lines in the figure) to provide a non-contractible area wherein the contraction force does not act, whereas the portions of the elastic members 25, 26, 28 extending laterally from the non-contractible area provide contractible areas wherein the contraction force acts (i.e., the portions of the under-waist elastic members 25 and the curved elastic members 26, 28 remaining unintermittently). This assists in avoiding unwanted contraction in the width direction of the inner member (in particular, the absorber body 13). It is indisputable that the under-waist elastic members 25 and the curved elastic members 26, 28 may be disposed unintermittently across the inner member 10 as shown in FIG. 6.

The outer member 20 discussed above may be manufactured using the technologies disclosed, for example, in JP H04-28363 A or JP H11-332913 A. The curved elastic members 26, 28 may be cut on the inner member 10 into an intermittent state preferably using the cutting method disclosed in JP 2002-035029 A, JP 2002-178428 A, or JP 2002-273808 A.

Unlike the illustrated embodiment, the curved elastic members 26, 28 may be provided in only either one of the front body section F and the back body section B. On the other hand, with the curved elastic members 26, 28 in both the front body section F and in the back body section B, an embodiment (not shown) may be also conceivable in which part or all of a group of curved elastic members 28 arranged on the front body section F side intersects with part or all of a group of curved elastic members 26 arranged on the back body section B side, but the embodiment as illustrated is preferred, in which the group of curved elastic members 28 arranged on the front body section F side and the group of curved elastic members 26 arranged on the back body section B side do not intersect with each other, and are arranged longitudinally spaced apart from each other in the middle in the front-back direction, in particular, in the area slightly closer to the front body section F.

The stretch rates of the elastic members 24 to 28 in the fixed states may suitably be decided. For ordinary adult diapers, the stretch rate of the waist elastic members 24 may be about 160 to 320%, that of the under-waist elastic members 25 may be about 160 to 320%, and that of the curved elastic members 26, 28 may be about 230 to 320%.

Cover Sheet

As shown in FIGS. 1 and 3, cover sheets 50, 60 may be disposed for covering the front and back end areas of the inner member 10 fixed on the interior face of the outer member 20 and for preventing leakage through the front and back edges of the inner member 10. Discussing the illustrated embodiment in further detail, front cover sheet 50 extends from the interior face of the folded portion 20C in the waist end area onto the front end area of the inner member 10 over the entire width on the interior face of the front body section F, whereas the back cover sheet 60 extends from the interior face of the folded portion 20C in the waist end area onto the back end area of the inner member 10 over the entire width on the interior face of the back body section B. The folded portions 20C formed by folding the outer member 20 onto the interior face of the diaper may be extended onto the inner member 10 until they overlap, to thereby form the portions equivalent to the cover sheets 50, 60 in the illustrated embodiment. Further, each cover sheet 50, 60 may be located outward of the folded portion 20C in the waist end area, i.e., between the presser sheet 20A and the folded portion 20C.

Sheet Layers Constituting Outer Member

As shown in FIGS. 3 and 7(*a*) to 10(*a*), the number of stacked sheet layers differs in different areas of the outer member 20. Specifically, the outer member 20 shown in FIG. 7(*a*) has longitudinally varying number of stacked sheet layers, that is, three layers in zone p, four layers in zone q, three layers I zone r, and two layers in zone s, and each boundary at which the number of layers changes is referred to as a stacked sheet number change part 62. The layered structure is such that, for example, in the area q shown in FIG. 7(*a*), which has the largest number of layers in the present embodiment, located outermost (on the side of the face out of contact with the skin) is the backing sheet 20B, located inside thereof are the presser sheet 20A and the folded portion 20C in this order, the folded portion 20C being an extension of the backing sheet 20B folded along the waist opening edge onto the interior face, and located innermost (on the side of the face to be in contact with the skin) is the front cover sheet 50 in the front body section F and the back cover sheet 60 in the back body section B, with the number of staked layers being four in total. In this way, in the outer member 20 in the illustrated embodiment, the number of stacked sheet layers varies from the waist opening to the leg openings such that three layers in the zone p, four layers in the zone q, three layers in the zone r, and two layers in the zone s, with three stacked sheet number change parts 62 present between the zones p and q, between the zones q and r, and between the zones r and s, in total. The structure of the outer member 20, such as the number or order of the sheets constituting the layers, is not limited to the illustrated embodiment and may suitably be modified, as long as at least one stacked sheet number change part 62 is present.

Structure of Cut

In FIGS. 7 to 10, figures (a) are sectional views taken along lines 7-7 and figures (b) are views seen from the ventral side, in the vicinity of the cuts in the underpants-type disposable diaper.

Referring to FIGS. 7 to 10, cuts 61 are discussed.

FIG. 7 shows cuts in the first embodiment. As shown in FIG. 7(*b*), each cut 61 extends in the longitudinal direction, is located adjacent on the central side in the width direction of a side seal 21, and extends longitudinally across a stacked sheet number change part 62 in the outer member 20. In the embodiment shown in FIG. 7(*a*), as discussed above, the number of stacked layers varies from the waist opening longitudinally downwards to the leg openings such that three layers, four layers, three layers, and two layers in the zones p, q, r, and s, respectively, in each of the front body section F and the back body section B. Three stacked sheet number change parts 62 in total are present in the outer member 20, i.e., between the zones p and q, between the zones q and r, and between the zones r and s. The force longitudinally tearing the side seal 21 tends to turn transversely at these positions to develop transverse tearing. In the light of this, by cutting longitudinally all the sheet layers present in the thickness direction in each stacked sheet number change part, the side seal tends to be torn off or ripped down in the longitudinal direction without transverse tearing, so that smooth longitudinal tearing of the side seal 21 is facilitated.

The tearing off or ripping down in the stacked sheet number change part 62 is characterized by the tendency of the longitudinally tearing force proceeding along the side seal to turn to proceed transversely along the stacked sheet number change part, particularly where the number of stacked sheets varies from smaller to larger number, among the positions where the number of stacked sheet layers varies, which leads to development of transverse tearing at the stacked sheet number change part 62. Tearing from the waist opening longitudinally downwards to a leg opening is particularly vulnerable to the transverse tearing in the stacked sheet number change part 62 at the boundary between the zones p and q, where the number of stacked sheets changes from three to four, whereas tearing in reverse from a leg opening longitudinally upwards to the waist opening is particularly vulnerable to the transverse tearing in the stacked sheet number change part 62 at the boundary between the zones r and q. The presence of cuts 61 in the stacked sheet number change parts 62, where the transverse tearing is prone to proceed, smoothly facilitates longitudinal tearing of the side seal 21. Longitudinal tearing of the side seal 21 may be carried out either from the waist opening longitudinally downwards to a leg opening or from a leg opening longitudinally upwards to the waist opening.

Further, in the outer member 20 of the first embodiment, no perforated line extending from the waist opening to a leg opening is formed in the vicinity of the side seals 21, but the cuts 61 are formed only in the stacked sheet number change parts 62, where the transverse tearing is prone to develop, and no cut 61 is formed anywhere other than the stacked sheet number change parts 62 (no cut is formed without longitudinally cutting across a stacked sheet number change part 62), which results in less cuts brought into contact with the skin, better fitting when worn, and less likelihood of leakage through cuts, compared to underpants-type disposable diapers having perforated lines. In addition, when there are a plurality of staked-sheet-count transition positions 62, the cut 61 may not necessarily be provided in every position 62, and part of the stacked sheet number change parts 62 (e.g., less vulnerable to transverse tearing) may not be provided with the cut 61. Each cut 61 shown in FIG. 7(*b*) has a longitudinal dimension 61L of preferably 2 mm to 10 mm, more preferably 4 mm to 8 mm, which may suitably be decided otherwise. The distance 61W in the width direction between the side seal 21 and the cut 61 is preferably 0 mm to 5 mm, more preferably 1 mm to 3 mm, which may suitably be decided otherwise. In view of prevention of transverse tearing, each cut 61 preferably penetrates all the layers constituting the outer member 20 as shown in FIG. 7(*c*).

FIGS. 7 to 10 show the embodiments wherein the number of the stacked layers is three in the zone p, four in the zone q, three in the zone r, and two in the zone s, but the present invention is not limited to these as discussed above and, even with the number of the stacked layers other than the above, the transverse tearing may be avoided with the cuts 61 extending longitudinally across the stacked sheet number change parts 62 as in the first embodiment.

It is preferred that a pair of cuts 61 is provided one in the front body section F and the other in the back body section B since, in tearing by the wearer of the side seals of the underpants-type disposable diaper, for example, the transverse tearing may be avoided even when nearly developing either in the ventral or dorsal section.

That said, it is conceivable to provide the cuts 61 only in the front body section F or only in the back body section B and, in this case, the cuts 61 may be provided either in the front body section F or the back body section B. Further, when the cuts 61 are provided both in the front body section F and in the back body section B, the cuts 61 in the front body section F may be arranged coincident with the cuts in the back body section B for ready production, but may be arranged at positions longitudinally or transversely displaced from those of the cuts in the back body section B.

FIG. 8 is a schematic view of the cuts 61 in the second embodiment. As each cut 61 is configured to extend closer to the side seal 21 with increasing proximity to its longitudinal ends, even when the force for longitudinally tearing off or ripping down the side seal 21 is turned transversely at the stacked sheet number change part 62 to develop transverse tearing, the force is guided along the cut 61 back toward the side seal 21, so that continuous tearing of the side seal is facilitated.

Further, irrespective of whether the side seal 21 is torn from the waist opening longitudinally downwards to a leg opening or the side seal 21 is torn in reverse from a leg opening longitudinally upwards to the waist opening, the opposed ends of each cut 61 are oriented toward the side seal 21, so that the tearing force is guided to the side seal 21 via the cut 61. In this way, the side seal 21 may be torn smoothly either from the waist opening longitudinally downwards to a leg opening or in reverse from a leg opening longitudinally upwards to the waist opening.

FIG. 8(*b*) illustrates the cuts 61 in a semicircular shape, but the cuts 61 are not limited to this shape, and may be doglegged with its ends oriented toward the side seal 21.

FIG. 9 illustrates the structure of a cut 61 in the third embodiment. The cuts 61 preferably penetrate all the sheet layers in the thickness direction of the outer member 20 for avoiding the transverse tearing, but it suffices that the cuts 61 penetrate all the sheet layers but one (i.e., the one sheet layer has no cut) as in this third embodiment. In the embodiment shown in FIG. 9(*b*), only the innermost (on the side of the face to be in contact with the skin) front cover sheet 50 and back cover sheet 60 are without the cut, and all the remaining sheet layers have the cut in the stacked sheet number change part 62.

The sheet layer without the cut may suitably be decided. For example, of the four layers of sheets constituting the zone q of the outer member 20, it is conceivable to cut the two outer layers, leaving the two inner layers, i.e., to cut the presser sheet 20A and the backing sheet 20B, leaving the front or back cover sheet 50, 60 and the folded portion 20C uncut. Alternatively, of the four layers of sheets constituting the zone q of the outer member 20, it is conceivable to cut one outer layer, leaving the three inner layers, i.e., to cut only the backing sheet 20B, leaving the front or back cover sheet 50, 60, the folded portion 20C, and the presser sheet 20A uncut.

As in this third embodiment, forming the cut 61 through all the sheets but one of the outer member 20 will result in excellent appearance when the diaper is worn, as the skin is not observable through the cut 61 in the outer member 20. Further, as in the illustrated embodiment, with the innermost (on the side of the face to be in contact with the skin) sheet layer free of the cuts 61, no cut 61 is present in the sheet which is to be in direct contact with the skin of the wearer, which provides better fitting compared to the diapers wherein the cuts 61 are brought into contact with the skin. In the illustrated embodiment, all the cuts 61 are covered with the innermost sheet layer, but it suffices that only a part of the cuts 61 is covered with the innermost sheet layer.

FIG. 10 is a schematic view of the cuts 61 in the fourth embodiment. Specifically, in the fourth embodiment, a dent 21U concaved laterally is formed in the side edge of the side seal 21 on the central side in the width direction WD so as to longitudinally cross a stacked sheet number change part 62, and the cut is formed in the dent. More specifically, in the embodiment shown in FIG. 10(*b*), dents 21U are formed by making shorter the width of transversely-elongate rectangular melt-bonded areas 21*m* located on the stacked sheet number change parts 62 of the outer member 20 compared to the width of the remaining melt-bonded areas 21*m*, and a longitudinal cut 61 is formed in each dent. Each cut 61 has a longitudinal dimension 61L of preferably 2 mm to 10 mm, more preferably 4 mm to 8 mm, which may suitably be decided otherwise. The distance 61W in the width direction between the side seal 21 and the cut 61 is preferably 0 mm to 5 mm, more preferably 1 mm to 3 mm, which may suitably be decided otherwise. Each dent 21U has a longitudinal dimension 21L 100% to 150% the longitudinal dimension 61L of the cut 61, and a dimension 21W in the width direction 100% to 200% the distance 61W in the width direction between the side seal 21 and the cut 61, which may suitably be decided otherwise.

In this embodiment, the cuts 61 are present within the entire width of the side seals 21, which results in excellent appearance when the diaper is worn, and excellent wear comfort as the cuts are not brought into direct contact with the skin when the diaper is worn. In addition, transverse tearing will hardly proceed toward the center in the width direction of the outer member 20, and smooth, continuous longitudinal tearing is facilitated.

In any of the first to fourth embodiments, an auxiliary cut may be provided adjacent on the central side in the width direction of the cut 61 (i.e., a plurality of cuts may be provided at intervals in the width direction). The auxiliary cut may be in a longitudinally linear shape as in the first embodiment, or in a semicircular or doglegged shape with its ends oriented toward the side seal as in the second embodiment, as long as it extends longitudinally across the stacked sheet number change part 62. Further, the auxiliary cut may penetrate all the sheet layers constituting the outer member 20, or all the sheet layers but at least one. Even when a transverse tearing developed in the stacked sheet number change part 62 does not stop at the cut 61 but proceeds further centrally in the width direction of the outer member 20 along the stacked sheet number change part 62, the presence of the auxiliary cut in the way of the transverse tearing will stop the transverse tearing and assists in guiding the tearing force back to the side seal 21. In this context, the auxiliary cut is preferably positioned not too far from the cut located closest to the side seal (e.g., with the spaced distance in the width direction of 3 mm or less). Further, the auxiliary cut preferably has a longitudinal dimension larger than that of the cut located closest to the side seal.

To any of the various embodiments discussed above, structures of other embodiments may suitably be combined.

Explanation of Terms in the Specification

The following terms appearing in the present specification shall have the following means unless otherwise specified herein.

- The "front-back direction" refers to the direction shown by the reference sign LD (longitudinal direction) in the figures, whereas the "width direction" refers to the direction shown by the reference sign WD (transverse direction) in the figures, and the front-back direction and the width direction are orthogonal to each other.

The "spread state" refers to the state in which an article is spread flatly without contraction (including any contraction, such as contraction by means of elastic members) or slack.

The "stretch rate" refers to a value with respect to the natural length being 100%. For example, a 200% stretch rate is synonymous with stretch in two folds.

The size of each part refers to the size not in the natural length state but in the spread state, unless otherwise specified.

INDUSTRIAL APPLICABILITY

The present invention is applicable to underpants-type disposable wearing articles, such as underpants-type disposable diapers including the above-discussed embodiments, underpants-type disposable sanitary napkins, and underpants-type disposable diaper covers.

DESCRIPTION OF REFERENCE SIGNS

10: inner member
11: top sheet
12: liquid-impervious sheet
13: absorber body
14: packing sheet
15: gathered sheet
16: gathering elastic member
20: outer member
20A: presser sheet
20B: backing sheet
20C: folded portion
21: side seal
21*m*: melt-bonded area
21U: dent
21L: longitudinal dimension of dent
21W: transverse dimension of dent
23: vicinity of waist opening
24: waist elastic member
25: under-waist elastic member
26: dorsal curved elastic member
28: ventral curved elastic member
29: round-leg line
50: front cover sheet
60: back cover sheet
61: cut
61L: longitudinal dimension of cut
61W: distance in width direction between side seal and cut
62: stacked sheet number change part
B: back body section
BS: three-dimensional gather part
F: front body section
WD: width direction
LD: longitudinal direction

The invention claimed is:

1. An underpants-type disposable wearing article, comprising:

a front body section and a back body section, opposed side seals formed by joining the front body section and the back body section together along opposed lateral portions by means of melt-bonding, a waist zone cylindrically continuous via the side seals, a waist opening, which is an opening on a waist side of the waist zone, and a pair of right and left leg openings located closer to legs than the waist zone, wherein the front body section and the back body section are formed by bonding a plurality of sheet layers, each side seal and area adjacent on a central side in a width direction thereof have at least one stacked sheet number change part where a number of stacked sheets varies from a waist opening side toward a leg openings side, wherein a cut extending longitudinally across the at least one stacked sheet number change part is formed adjacent on the central side in the width direction of each side seal in the sheet layers forming at least either the front body section or the back body section, and wherein the disposable article is free of a perforated line intended for splitting from the waist opening to a leg opening.

2. The underpants-type disposable wearing article according to claim 1, wherein each cut is configured to extend closer to the side seal with increasing proximity to its longitudinal ends.

3. The underpants-type disposable wearing article according to claim 2, wherein the cuts consist of cuts each penetrating all but one of the plurality of sheet layers constituting the front body section or the back body section.

4. The underpants-type disposable wearing article according to claim 2, wherein a dent concaved laterally is formed in a side edge of each side seal on the central side in the width direction so as to cross longitudinally one stacked sheet number change part, and wherein each cut is formed in each dent.

5. The underpants-type disposable wearing article according to claim 1, wherein the cuts consist of cuts each penetrating all but one of the plurality of sheet layers constituting the front body section or the back body section.

6. The underpants-type disposable wearing article according to claim 1, wherein a dent concaved laterally is formed in a side edge of each side seal on the central side in the width direction so as to cross longitudinally one stacked sheet number change part, and wherein each cut is formed in each dent.

7. The underpants-type disposable wearing article according to claim 5, wherein a dent concaved laterally is formed in a side edge of each side seal on the central side in the width direction so as to cross longitudinally one stacked sheet number change part, and wherein each cut is formed in each dent.

* * * * *